United States Patent
Kirk, III et al.

(10) Patent No.: US 9,486,829 B2
(45) Date of Patent: Nov. 8, 2016

(54) APPLICATOR

(75) Inventors: Karl Dallas Kirk, III, New York, NY (US); Paul J. Mulhauser, New York, NY (US)

(73) Assignee: OptMed, Inc., New York, NY (US)

( * ) Notice: Subject to any disclaimer, the term of this patent is extended or adjusted under 35 U.S.C. 154(b) by 849 days.

(21) Appl. No.: 13/488,389

(22) Filed: Jun. 4, 2012

(65) Prior Publication Data

US 2013/0004230 A1    Jan. 3, 2013

Related U.S. Application Data

(60) Provisional application No. 61/493,426, filed on Jun. 4, 2011.

(51) Int. Cl.
| | | |
|---|---|---|
| *B05C 17/00* | (2006.01) | |
| *A45D 34/04* | (2006.01) | |
| *A61M 35/00* | (2006.01) | |

(52) U.S. Cl.
CPC ............... *B05C 17/00* (2013.01); *A45D 34/04* (2013.01); *A61M 35/003* (2013.01)

(58) Field of Classification Search
CPC combination set(s) only.
See application file for complete search history.

(56) References Cited

U.S. PATENT DOCUMENTS

| | | | | |
|---|---|---|---|---|
| 1,910,669 | A | * | 5/1933 | Biederman .................... 401/263 |
| 2,896,237 | A | * | 7/1959 | Owens et al. ................. 401/262 |
| 2,921,324 | A | * | 1/1960 | Gibbons ........................ 401/263 |
| 4,225,255 | A | * | 9/1980 | Braun et al. ................... 401/137 |
| 5,971,645 | A | * | 10/1999 | Fukushima ............. A47L 25/08 401/183 |
| 6,340,097 | B1 | * | 1/2002 | D'Alessio ........... A61M 35/003 215/12.2 |
| 8,403,178 | B2 | * | 3/2013 | May et al. ..................... 222/129 |

* cited by examiner

*Primary Examiner* — David Walczak
(74) *Attorney, Agent, or Firm* — Edward K. Welch, II; IP&L Solutions

(57) ABSTRACT

An improved applicator for dispensing liquids and viscous fluids comprising an applicator body, an applicator tip or applicator assembly, and optionally a filter element wherein the applicator tip or assembly has at least one of several beneficial features including a receptacle for shards, a fluid rate controlling tip, and a bubble breaking design.

24 Claims, 5 Drawing Sheets

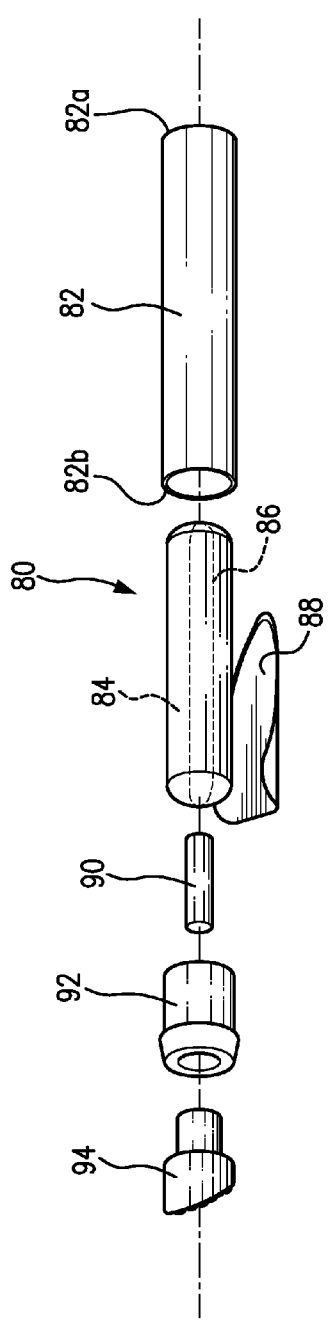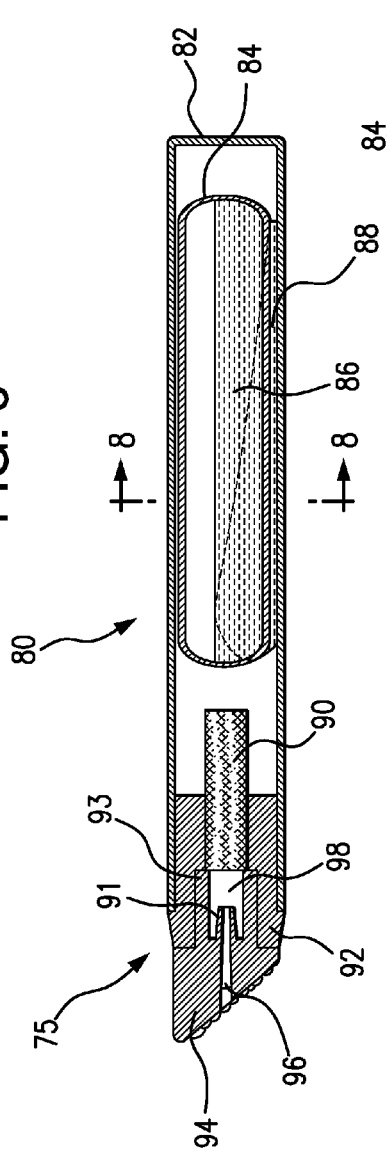

APPLICATOR

This Application claims of the benefit of U.S. Provisional Patent Application No. 61/493,426, filed on Jun. 4, 2011, the content of which is hereby incorporated herein by reference in its entirety.

The present invention pertains to improved disposable applicators for dispensing liquid and viscous fluid compositions, especially two-part reactive compositions, most especially two-part curable compositions. Though such applicators are and can be configured for use in mechanical devices, they are also capable of manual, hand-held use.

BACKGROUND

Hand-held, single use/unit dose applicators are well known and have been used for decades. In their most generic embodiment they comprise a dual chambered applicator wherein either 1) a frangible dividing wall is formed in a tubular body having a closed end and an open end, which dividing wall isolates the content of the chamber defined by the closed end and the dividing wall from the open end or 2) one or more frangible ampoules is located within the lumen of a tubular body having a closed end and an open end. In use, the frangible element is subjected to pressure to crush the dividing wall or ampoule so as to release and make available for dispensing, the contents therein.

These applicators further comprise an applicator tip having a distal end sealingly engaged with the open end of the tubular body and a proximal end from which the contents of the applicator is be dispensed and applied to whatever substrate is to be treated. According to certain embodiments in the art, the tip may be a porous tip whereby the porosity of the tip itself serves to filter the shards of the dividing wall or ampoule formed when the dividing wall or ampoule is crushed as the contents are dispensed. Other embodiments, especially those wherein the applicator tip is non-porous and relies upon one or more distinct flow paths, typically a lumen or bore along the longitudinal axis thereof, through the applicator tip from its distal end associated with the open end of the tubular body to the face of the applicator tip for dispensing the contents of the applicator, employ a filter element interposed between the applicator tip and the dividing wall or ampoule. The filter element prevents the shards from passing into the lumen of the filter tip and being dispensed with the contents of the applicator.

Over the years, these applicators as well as different elements thereof have been modified, redesigned, and/or reconfigured all in an effort expand their utility as well as their overall performance. Certain of these modifications are dependent upon the specific materials to be dispensed whereas others have broader applicability. Perhaps the most prolific in this regard are the inventors of Closure Medical Corporation. Closure Medical has made improvements in relation to the applicator tips, the integration of a curative in the applicator tip, the use of protective films to prevent the piercing of the container body by shards created by the crushing of an ampoule, and so on, all as will be discussed in greater detail below.

Despite all the improvements to date, there still remain a number of issues with respect to the state of the art applicators, especially as they relate to the dispensing of curable compositions. For example, state of the art applicators either allow for the passage of shards, particularly small shards, of the ampoules or, more commonly, are configured whereby the shards build up on the filter whereby flow of the curable composition past the shard build up is prevented or greatly reduced. In another aspect, the flow of materials is difficult to control due to the pressure needed to force the contents of the applicator through the filter. In yet another aspect, many of the two-part compositions place the second part in the applicator tip or the filter element; however, this results in the initial flow of the first part through the applicator tip or filter element being highly activated while the latter flow is poorly activated, perhaps so poorly that it fails to cure or cures so slowly as to be inappropriate for the given application. Additionally, in those instances which employ a porous applicator tip, it is not possible to place the second component in the lumen of the applicator body as it will inherently saturate the porous applicator tip, if not leak out. Further, the applicators of the prior art have a tendency to introduce bubbles into the composition being dispensed. In compositions having a water-like viscosity this is not an issue since the bubbles tend to break upon emanating from the dispenser tip; however, this is not so for more viscous materials, especially not for curable compositions which are already activated in the applicator and, consequently, whose viscosity is already increasing as it is being dispensed.

Accordingly, there is a need for an applicator having a dual chamber, whether as distinct chambers separated by a frangible dividing wall or as a frangible ampoule within the applicator body or a combination of both, wherein the shards of the crushed dividing wall or the ampoule are not dispensed with the fluid and do not block the flow of the liquid or viscous fluid to be dispensed.

There is a need for an applicator which enables greater control of the rate at which the content of the applicator is dispensed.

There is a need for an applicator of a two-part curable composition which allows for a more uniform activation of the curable composition. In particular, there is a need for an applicator which allows for more uniform activation while also avoiding concerns with respect to leakage or the need for a closure element.

Furthermore, there is a need for an applicator which avoids or at least minimizes the presence of bubbles in the dispensed liquid or viscous fluid composition.

SUMMARY

The present invention pertains generally to improvements in the design, function and elements of a hand-held dual chambered applicator for liquids and viscous fluids and liquid and viscous fluid compositions (hereinafter altogether referred to as the "liquid composition"). Conventionally, such applicators comprise a dual chambered tubular applicator body having a closed distal end and an open proximal end and either a dividing wall in the lumen of the applicator body separating the two chambers or an ampoule placed within the lumen of the applicator body. The applicators also comprise an applicator tip having a dispensing orifice on its applicator face and a central lumen or bore through which the liquid composition is fed from the applicator body to the orifice. The distal end of the applicator tip is inserted into the open end of the applicator body, thereby closing the open end of the applicator body. In the case of a non-porous applicator tip, though it may be present with a porous applicator tip as well, a filter element resides intermediate the applicator tip and the contents of the applicator body which filter element prevents shards of the crushed dividing wall or ampoule from being dispensed with the fluid composition.

According to a first aspect, the present application provides for a dual chambered applicator having a filter element for preventing the dispensing of shards of the crushed dividing wall or ampoule wherein the filter is in the form of a cylindrical filter element whose diameter is considerably smaller that the inner diameter of the lumen of the applicator body so as to create a tubular shaped space between the filter and the applicator body which space serves as a receptacle of the shards. The cylindrical filter element is retained in a corresponding cylindrical recess in the distal end of the applicator tip.

According to a second aspect, the present application provides for an applicator tip which provides for greater control of the flow rate of the liquid composition being dispensed. Specifically, according to this aspect of the present application the applicator tip is provided with a longitudinal passageway or lumen extending from the distal end of the applicator tip to an orifice in the applicator face wherein the lumen is conical in shape having a small diameter at the distal end and a considerably larger diameter at the orifice. Generally speaking, the area of the cross section of the cone at the orifice will be at least about twice, preferably at least about three times, more preferably at least about 4 times that of the cross section at the distal end of the lumen. The broadening of the lumen slows the rate of flow for the same pressure for better control in the dispensing of the liquid composition at the tip orifice.

According to a third aspect, the present application provides for an applicator tip which prevents or markedly reduces the formation of bubbles in the liquid composition being dispensed. What remaining bubbles are expelled through the applicator tip are comparatively large and readily break upon emerging from the orifice of the applicator tip. Specifically, according to this aspect of the present application, the applicator tip has one or more chambers immediately following a constricted flow path which transition allows for the breaking or coalescing of the bubbles into larger bubbles which readily break upon emerging from the orifice. In one embodiment, the chamber is a spherical chamber in the lumen or bore of the applicator tip. In a second embodiment, the chamber is a cylindrical recess in the distal end of the applicator tip which recess has a diameter smaller than the diameter of the filter element, which filter element may, itself, have a diameter smaller than the lumen of the applicator body, as in the preceding paragraph, or it may have a diameter the same as or substantially the same as that of the lumen of the applicator body. Finally, the applicator tip may have both of these features.

According to a fourth aspect, the present application provides for an applicator tip pin which prevents the accidental dispensing of the liquid composition during storage and handling. The tip pin has a body and a stem, the latter having a bulbous terminus at its distal end which corresponds in shape and diameter to a spherical chamber in the lumen or bore of the applicator tip. Thus, upon insertion of the tip pin into the orifice of the applicator tip, the bulbous terminus will encounter a slight interference fit with the walls of the lumen before emerging into the spherical chamber into which it will snap fit; thereby mechanically locking the tip pin in place.

According to a fifth aspect, the present application provides for an applicator for a two part liquid composition wherein a first part is contained within a frangible ampoule within the lumen of the applicator body and the second part, also a liquid or at least initially a liquid, is contained by capillary action solely or substantially solely between the outer surface of the ampoule and the inner wall of the applicator body. In any event, any amount of the second component that is not held by capillary action is insufficient to flow on its own. Preferably, the longitudinal dimensions of the ampoule and the applicator body are such that following assembly of the applicator, there is minimal room for lateral movement of the ampoule within the applicator body along its longitudinal axis. Similarly, the outer diameter of the ampoule is slightly smaller than the inner diameter of the applicator body such that the capillary action will manifest and hold the liquid in place.

Finally, according to a sixth aspect, the present application provides for an applicator for a two-part liquid composition comprising all of the above-referenced elements.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means, instrumentalities and combinations particularly pointed out in the appended claims.

DETAILED DESCRIPTION OF THE DRAWINGS

FIG. 6 is an exploded view of a third embodiment.

FIG. 7 is a cross-sectional view of the embodiment of FIG. 6 taken along the longitudinal axis thereof.

FIG. 8 is a cross sectional view of the embodiment of FIG. 7 taken along the line 8-8.

Figure 1:
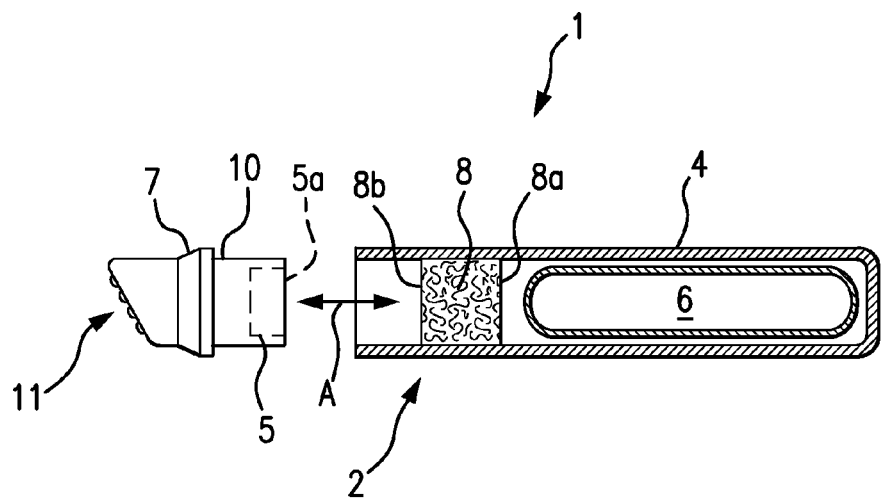
FIG. 1 is a partially exploded view of a first embodiment.
Figure 11:
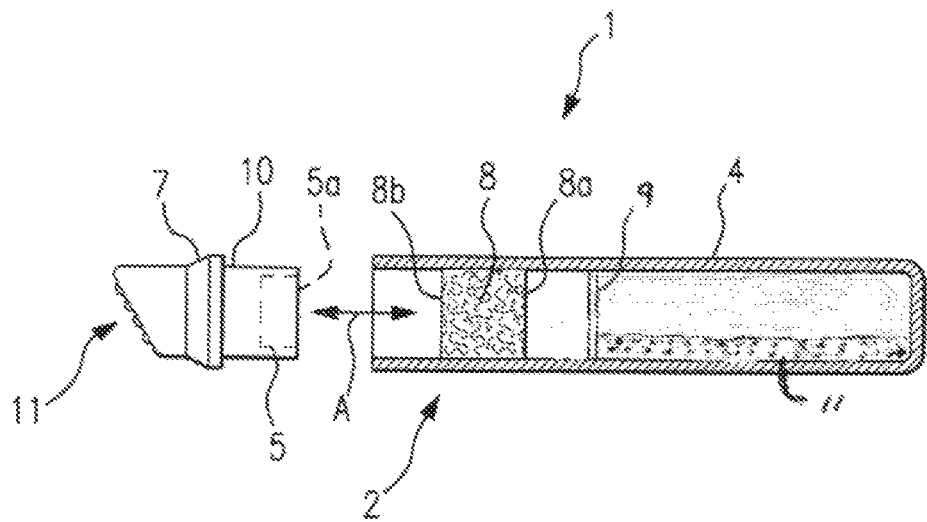

FIG. 11 presents an alternate embodiment of the applicator of FIG. 1 wherein a frangible wall replaces the ampoule.

Figure 2:
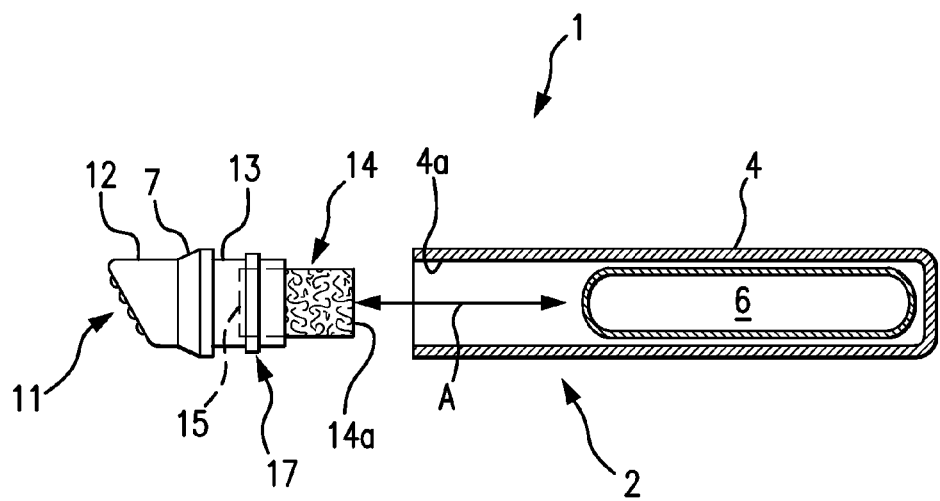
FIG. 2 is a partially exploded view of a second embodiment.
Figure 12:
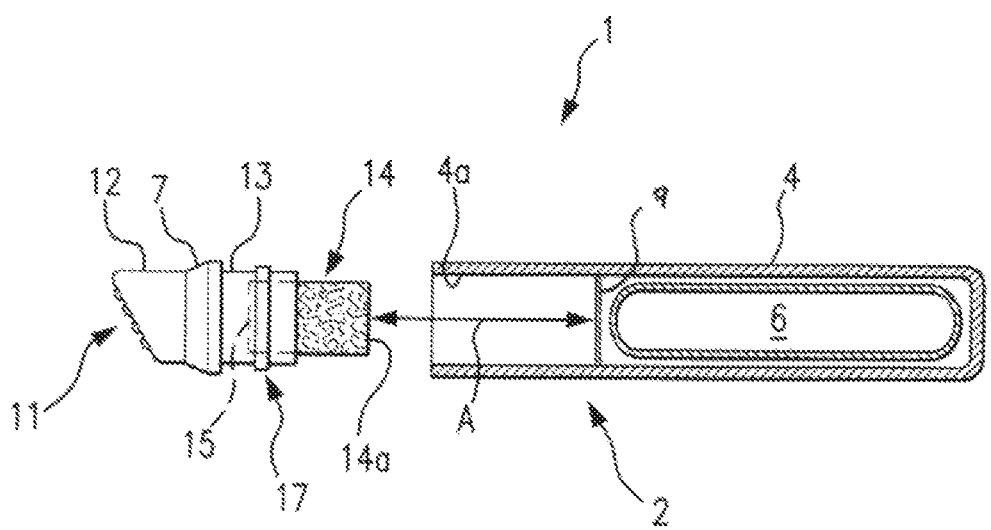

FIG. 12 presents an alternate embodiment of the applicator or FIG. 2 further comprising a frangible.

DETAILED DESCRIPTION OF THE PREFERRED EMBODIMENTS

In the following description, unless otherwise stated, it is to be understood that the applicator and the elements thereof are all essentially cylindrical in shape and all share the same longitudinal or cylinder axis. However, it is also to be understood that applicators and/or one or more of the elements thereof could be modified to have different cross-sectional shapes, such as elliptical, ovoid, rectangular, square, hexagonal, etc., and are within the teachings of this specification. In following, the term "lumen" in relation to the interior of the applicator is intended to refer to the space, whether of tubular shape or otherwise. Further, it is to be noted that for ease of understanding, the orientation and features of the applicator as well as the components thereof are referenced in terms of distal and proximal ends or regions as well as their orientation relative to the longitudinal axis of the applicator. The proximal end of the applicator is that end associated with the tip for dispensing the components within the applicator and the distal end is that closed end defining the bottom or sealed end of the container body. In following, the proximal end of an element of the applicator is that end which is closest to the proximal end of the applicator and the distal end is that end closer to the distal end of the applicator, both taken along the longitudinal axis of the applicator.

Generally speaking, the present teachings are directed to multiple features and elements of an applicator for the dispensing and application of liquid or viscous fluids which features or elements individually improve the performance of the applicator as a whole and which, in combination, add versatility of performance as well as added benefits and improved performance overall. The present teachings are especially applicable to those applicators having a dual chamber, whether as distinct chambers or compartments separated by a frangible dividing wall or as a frangible ampoule within the applicator body. In those embodiments having the frangible dividing wall, the distal most chamber or compartment is a sealed compartment. Applicators having such multiple chambers or compartments in the applicator body are especially suited for single use or unit dose applications.

In addition to its application to known applicators having a frangible wall or a frangible ampoule, the present teachings are also applicable to applicators having both a frangible wall and a frangible ampoule, the combination of which is believed previously unknown. Here the ampoule sits in one of the compartments defined by the frangible wall, preferably the sealed compartment.

According to a first aspect there is provided an improved filter design and arrangement for use with dual chambered applicators. FIG. 1 shows an exploded view of an applicator 1 whose filter arrangement depicts a conventional arrangement wherein a filter plug 8 is inserted between the ampoule 6 and the applicator tip element 10 in lumen of the applicator body 4. FIG. 2, on the other hand, depicts a cylindrical filter element whose diameter is considerably smaller than the inner diameter of the applicator body 4 such that a space 19, as more clearly shown in FIG. 4, remains between the side walls of the filter element and the inner surface of the applicator body. The space 19 serves as a receptacle for shards of the crushed ampoule or dividing wall which will tend to fall or move into the space 19 leaving the end 14a of the filter 14 clear of debris. This contrasts with the filter element 8 of FIG. 1 wherein the shards will build up on the inner surface 8a of the filter element 8, either blocking flow or severely restricting or inhibiting flow into and thought the filer element.

Preferably, the filter element is an elongated element, i.e., one whose length is greater than its width or diameter. Most preferably, the length of the filter is at least twice as long as its width. The filter elements themselves may be of various forms and types suitable for isolating a liquid or viscous fluid from glass fragments and particles. Preferably, the filter element is a porous plastic material having fine and/or tortuous pathways through the body of the filter. However, other filters are also possible. For example, if a high rate of flow is desired, the filter could be in the form of a solid or perforated tube. While the majority of shards will be caught in the space between the tube and the applicator body inner wall, the lumen of the tube is kept small to prevent the passing of shards that may build up above the end of the filter element or which are merely caught in the flow of the liquid being dispensed. In this regard, the diameter of the lumen determines the filtering capability of the tubular filter element. Another option is to have a hollow tube 14, whose end 14a is either open or closed, and wherein a plurality of small perforations or bores exist through the wall and, if applicable, the end, into the lumen of the hollow tube filter element.

Alternate embodiments of the applicators of FIG. 1 and FIG. 2 are shown in FIG. 11 and FIG. 12, respectively. In FIG. 11, instead of the ampoule 6 of FIG. 1, the embodiment employs a frangible wall 9 which defines a sealed compartment containing a fluid 11. In the case of FIG. 12, the applicator body includes both the ampoule 6 and a frangible wall 9. The latter design is especially suited for those instances where a two-part liquid composition is to be dispensed, part of which is outside of the ampoule. Here the frangible wall ensures that the liquid outside of the ampoule does not unintentionally leak out through the applicator tip.

It is to be noted that the filter element of this aspect of the present teachings requires a modest redesign of the applicator tip. Specifically, although not shown, the unitary, generally cylindrical applicator tip 10 of FIG. 1 has a bore through and along its longitudinal axis A which allows for the flow of the liquid through the filter, through the applicator tip and to the applicator face 11. But for the bore along the longitudinal axis, the applicator tip 10 is solid. In contrast, as shown in FIG. 2, the applicator tip 12 has a cylindrical recess 15 in its distal end which receives the proximal end of the filter element 14. Preferably, the fit is a snug or slight interference fit for easy assembly without concern that the filter will become dislodged from the recess 15. The applicator tip also preferably has a circumferential collar 7 about its midsection, taken along its longitudinal axis A, which collar acts as a stop to prevent the applicator tip from being inserted too far into the lumen of the applicator body 4.

Though not critical, the applicator tip 12 of FIG. 2 also has a circumferential band 17 protruding from the outer surface of the distal end of the applicator tip. The height of the band is minimal, just sufficient to create a snug or slight interference fit with the inner wall 4a of the applicator body 4 upon insertion of the applicator tip into the lumen of the applicator body along the longitudinal axis A.

Figure 3:
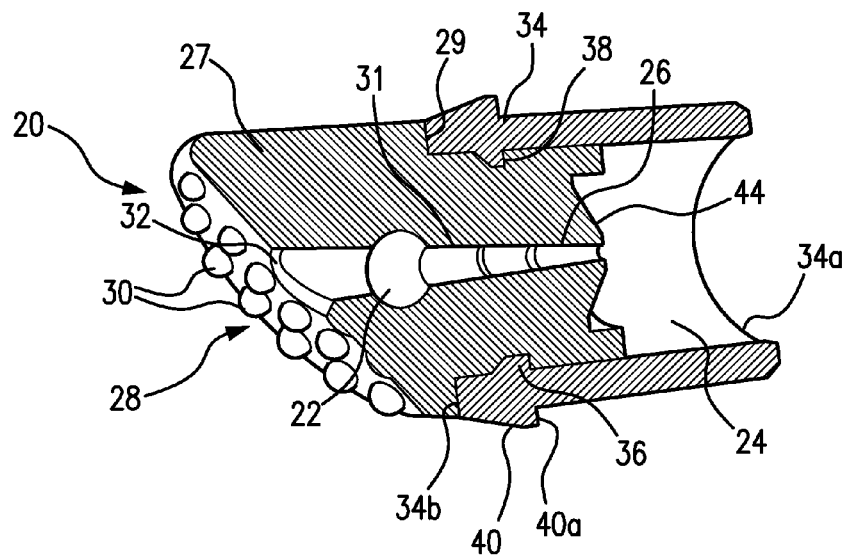
FIG. 3 is a cross-sectional view of the applicator tip of FIGS. 1 and 4.

Although shown as a single unit in FIG. 2, as shown in the embodiment of FIG. 3, the applicator tip may also comprise a two piece unit having a tip element 20 and an adapter element 34. The adapter element 34 is a hollow cylindrical element having a distal end 34a and a proximal end 34b, the former to be inserted into the lumen of the applicator body 4 and the latter having associated therewith a circumferential collar 40 having a distal surface 40a extending perpendicularly from the surface of the adapter element. The adapter element is to be inserted, distal end 34a first, into the lumen of the applicator body 4. The insertion is halted once the distal face 40a of the collar engages the open end of the applicator body 4.

The tip element 20 has a cylindrical distal end 26 and a cylindrical proximal end 27, with the former having a smaller diameter than the latter, the demarcation between the two evident by a stop wall 29 comprising the distal surface of the proximal end. This stop wall 29 engages the proximal end 34b of the adapter 34 (also the proximal face of the collar 40) upon insertion of the distal end of the tip element into the lumen of the proximal end of the adapter. Although the diameters of the distal end of the tip element 26 and of the lumen of the adapter element may be such as to provide for a snug or slight interference fit, it is also contemplated that the two elements may have integrated therein a locking mechanism. For example, as seen in FIG. 3, the distal end of the tip element may have an annular recess which engages an annular protrusion 36 on the inner surface of the lumen of the adapter. The annular protrusion may have a distal face 38 extending perpendicular to the surface of the adapter lumen which serves to lock the tip element and adapter element together. The annular protrusion 36 preferably has a ramped proximal face to facilitate the insertion of the tip element 20 into the lumen of the adapter 34: allowing the distal end of the tip element to slip past the annular protrusion.

According to a second aspect, there is provided and an applicator tip which provides for greater control of the flow rate of the liquid composition being dispensed. Specifically, as shown in FIGS. 3 and 7, the lumen 31 and 96 of applicator tip 20 and 94, respectively, has a conical cross-section taken along its longitudinal axis. FIG. 3 shows a tip further comprising a spherical chamber 22 located about midway along the lumen, which feature will be discussed further below. Pertinent to the present aspect is the conical shape of the lumen whose diameter, and hence cross-sectional area, at the dispensing orifice 32 on the face 28 of the applicator tip 20 is considerably larger than that at the distal end 26. Generally speaking, the area of the cross section of the cone, defined on the plane perpendicular to its longitudinal axis, at the orifice will be at least about twice, preferably at least about three times, more preferably at least about 4 times that of the of the cross section at the distal end of the lumen. Although the diameter could be sufficiently large as to result in a ten-fold or greater increase in the cross-sectional area, generally the increase will be ten-fold or less, preferably eight-fold or less. The broadening of the lumen slows the rate of flow for the same pressure on the exterior wall of the applicator body for better control in the dispensing of the liquid composition at the tip orifice.

According to a third aspect of the present teachings, there is provided an improved applicator tip which prevents or markedly reduces the formation of bubbles in the liquid composition being dispensed. Such bubbles may have arisen as a result of the agitation or shaking of the container, especially where the composition within the container is a two-part composition and one wants to ensure adequate mixing. Air bubbles also arise as the liquid flows through the filter and displaces the air in the interstitial spaces in the filter element. Of course, air is also present in the dispenser body and, if one rocks the container about its trans-axis, i.e., raising and lowering its distal end while concurrently lowering and raising its proximal end, it will once again introduce air into the filter region. Regardless, it is to be understood that when Applicant speaks of the breaking of air bubbles, what is actually happening is that small or tiny air bubbles are coalescing into larger bubbles which are readily passed out of the orifice of the applicator tip where they more readily break due to their large size.

Specifically, it has been found that the integration of one or more chambers into the applicator tip, especially immediately following a constricted flow path, allows for the breaking or coalescing of bubbles in the flow of the liquid composition into larger bubbles which readily break upon emerging from the orifice. Not intending to be bound by theory, it is believed the transition from a high pressure environment to a lower pressure environment occasioned by the chamber, with or without additional flow turbulence inducing features in or associated with the shape of the chambers, leads to the breaking and/or coalescing of the smaller bubbles. The presence of the chambers also provides for additional flow control as the pressure drop upon initial charging of the applicator dispensing flow path slows down the flow of materials so as to prevent premature glue ejection at the initial ampoule fracture and/or during excessively vigorous mixing.

According to a first embodiment of this aspect of the present teachings, as shown in FIG. 1, the chamber comprises a cylindrical recess 5 (depicted by broken lines) in the distal end of a one-piece applicator tip 10. On assembly, the proximal face 8b of the filter 8 engages the distal end 5a of the walls of the cylindrical recess 5, thereby creating the chamber defined by the cylindrical recess and the filter element 8.

A second embodiment of the bubble breaking chamber is shown in FIG. 7. Here the chamber comprises a cylindrical recess 98 in the distal end 93 of the tip element 94 of a two-piece applicator tip 75. Once again, the cylindrical recess has a diameter smaller than the diameter of the filter element 90. In this particular embodiment the applicator tip comprises a tip element 94 and a tip adapter 92, the adapter configured to hold the filter element 90 whose diameter is smaller than diameter of the lumen of the applicator body 82, all as described above in relation to the first aspect of the present teachings. In this particular embodiment, the tip element is shown as having a conical extension 91 protruding from the distal end of the tip element into the chamber 98 with the flow path 96 through the tip element originating at and longitudinally passing through conical extension. It is believed that the presence of this projection helps disrupt the flow path, creating turbulent fluid flow which, in turn helps decelerate the flow.

Third and fourth embodiments of the bubble breaking chambers are shown in FIG. 3. In the former, the chamber is in the form of a spherical chamber 22 disposed in the midsection of the flow path 31 of the tip element 20. The spherical chamber 22 has a diameter that is at least one and one-half times, preferably at least about two to three times, that of the flow path into which it is integrated at the point of its integration. Larger spherical chambers are possible, though, if a tip pin is to be employed, as discussed below, it is preferred that the diameter be within the ranges noted. In the case of a conical flow path, the diameter of the flow path is that which would have been present had the spherical chamber not been present, i.e., following the normal shape of the cone. Although FIG. 3 shows a conical flow path, as described above, it is also to be appreciated that according to this aspect of the present teachings the flow path may have a uniform diameter along its full length.

The fourth embodiment is that where both the spherical chamber 22 and the cylindrical recess 24 are present in the applicator tip or, as shown in FIG. 3, in the tip element. The use of both bubble breaking features merely provides added assurance in terms of the reduction in the presence of bubbles in the liquid composition to be dispensed. It is also to be noted that the distal face of the distal end of the applicator tip may be of a frustoconical shape 44 as also shown in FIG. 3.

Figure 4:
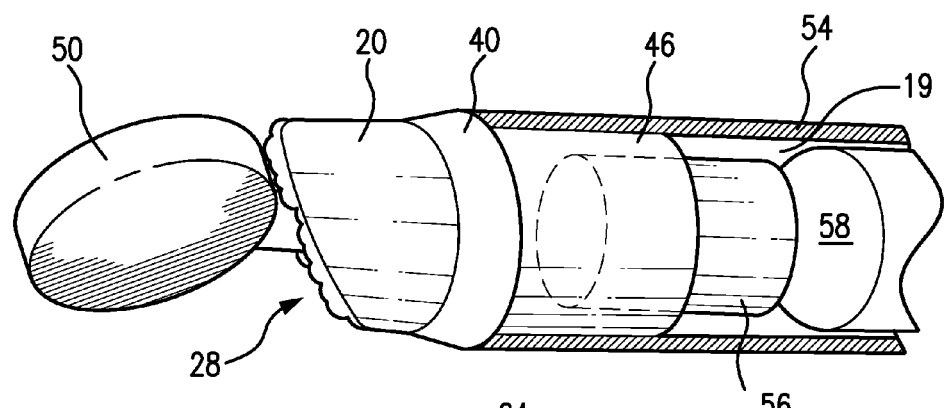
FIG. 4 is a partial view of an applicator tip with a closure pin.
Figure 5:
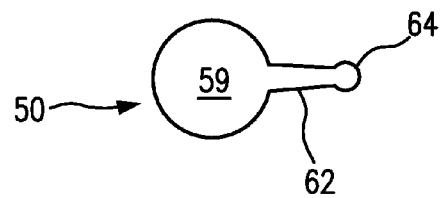
FIG. 5 is a cross-sectional view of just the closure pin of FIG. 4.

According to a fourth aspect, the present application provides for an applicator tip pin which prevents the accidental dispensing of the liquid composition during storage and handling. As shown in FIGS. 4 and 5, the tip pin 50 has a body 59 and a stem 62, the latter having a bulbous terminus 64 at its distal end which corresponds in shape and diameter to a spherical chamber in the lumen or bore of the applicator tip. Thus, upon insertion of the tip pin into the orifice of the applicator tip according to, e.g., FIG. 3, the bulbous terminus will encounter a slight interference fit with the walls of the lumen 31 of the tip element before emerging into the spherical chamber 22 into which it will snap fit; thereby mechanically locking the tip pin in place. Of course, it is also contemplated that the stem may have just a cylindrical or conical shape corresponding to the shape of the flow path through the applicator tip or tip element, as appropriate. In this case, the tip pin is merely forced into the tip orifice until it can no longer be moved. This forms a slight interference or compression fit with the inner wall of the flow path, thereby mechanically holding the pin in place. Further, while the body 59 of the pin is depicted as a disc, it could take any shape, but is preferably of a shape that one can easily grasp and remove.

According to a fifth aspect, the present application provides for an applicator for a two part liquid composition wherein a first part, part A, is contained within a frangible ampoule within the lumen of an applicator body and the second part, part B, also a liquid, or at least initially a liquid, is contained by capillary action between the outer surface of the ampoule and the inner wall of the applicator body. Specifically, FIGS. 6, 7 and 8 depict an applicator 80 embodying this aspect. Here the applicator 80 comprises an applicator body 82 having a closed end 82*a* and an open end 82*b*, an ampoule 84 containing a first liquid component 86 of a two-part composition, a quantity of a second component 88, a filter element 90, an applicator tip element 94 and an applicator tip adapter 92. As more clearly shown in FIG. 8, which presents a cross section of the applicator 80 at line 8-8, the ampoule 84 contains the first liquid component 86 and lies within the lumen of the tubular applicator body 82. A thin film of the second liquid component 88 lays between the inner wall of the lumen and the outer surface of the ampoule. This thin film is held in place by capillary action owing to the proximity of the diameter of the lumen to the diameter of the exterior wall of the ampoule. Generally speaking, the difference in diameters will not be greater than a couple millimeters, preferably a millimeter or less. Of course, where the viscosity of the second part, part B, is high, the capillary action is more difficult to break and, hence, somewhat greater diameter differences can be withstood as compared to, e.g., liquids with water like viscosities.

Additionally, in this aspect of the present teachings, it is preferred that the longitudinal dimensions of the ampoule and the lumen of the applicator body are such that following assembly of the applicator, there is minimal room for lateral movement of the ampoule within the applicator body along its longitudinal axis. If movement is allowed, it is generally insufficient to allow any significant amount of fluid to be retained by the inner wall of the lumen, as opposed to remaining in the interstitial space between the inner wall of the applicator body and the ampoule. In any event, any amount that is left behind will be insufficient to flow on its own and, thus, does not present a problem with leakage from the applicator through the applicator tip.

The present application also provides for a number of improved applicator devices comprising two or more of the above-referenced features, preferably all of the aforementioned features. For example, an applicator tip having both the conical passageway and one or more chambers, especially a spherical chamber in the passageway, provides an added benefit over that of either alone. Specifically, when one desires to stop the dispensing of the fluid, one releases the pressure on the sidewalls of the container body. This creates a pull-back or back-flow of the liquid into the container body. Because the applicator tip face has a film of the liquid on it, as the pull-back occurs, it brings this film with it, but with intervening air pockets (similar to what one sees when drinking the last of a beverage through a straw). When one then squeezes the container body to reinitiate dispensing, those film walls in the lumen of the passageway through the applicator tip move towards the orifice and produce a bubble upon being expelled from the orifice. However, though not intending to be bound by theory, it is believed that the conical passageway and the chamber cause the film to spread out as it moves towards the orifice so that it breaks before reaching the orifice, thereby preventing the formation of the bubble. This effect is also seen, but to a lesser extent, with just the conical flow path or the spherical chamber. Similar attributes and benefits are realized by using other combinations of the novel aspects of the present teachings.

Figure 9:
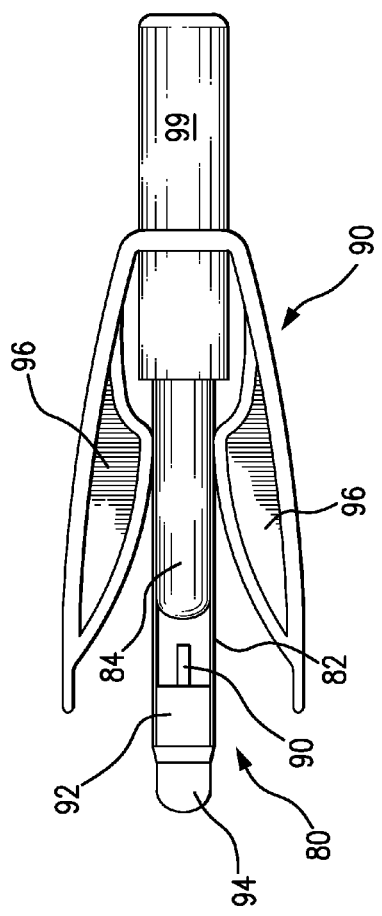
FIG. 9 is a top view of the applicator of FIG. 7 in an applicator handle.
Figure 10:
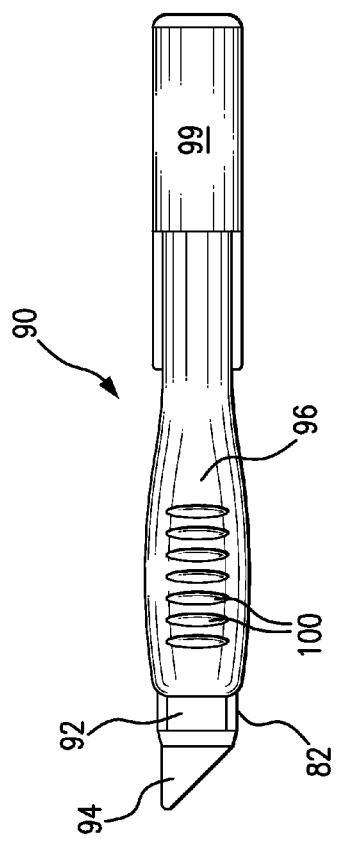
FIG. 10 is a side view of the assembled applicator and handle of FIG. 9.

Finally, the present teachings also provide for an improved applicator device comprising the fully assembled applicator according to the present teachings in a hand held dispenser handle. For example, as depicted by FIGS. 9 and 10, the present teachings provide for an applicator according to FIG. 7 in a dispenser handle 90. The dispenser handle comprises a body 99 and a pair of opposed handle elements 96, the opposing handle elements when pressed towards one another act upon the exterior wall of the applicator body 82 and, in turn, the ampoule 84 within the applicator body. FIG. 10 shows the device of FIG. 9 rotated 90° about its longitudinal axis. As indicated, the exterior surface of the handle elements 96 has a textured region 100 corresponding to the press pad where the thumb and forefinger of the user are to grasp the device. Although this is but one embodiment of a handle that may be used with the applicators of the present teachings, it is a preferred embodiment and is the subject of our co-filed provisional patent application entitled "Dispenser Handle", filed under Ser. No. 61/493,425, the contents of which are hereby incorporated herein in its entirety by reference.

Having described the improved applicators in terms of the five features and their respective embodiments above, attention is now turned to the more general aspects thereof. In this regard, it is to be appreciated that each of the novel features discussed above may be integrated into any of the state of the art applicators, either individually, in combination of two or more, or all together. State of the art applicators are well known. Exemplary of the state of the art applicators are: Badejo et. al.—U.S. Pat. No. 5,981,621, U.S. Pat. No. 6,565,840, U.S. Pat. No. 6,676,322 and US 2005/0147457 A1; Balance et. al.—U.S. Pat. No. 6,439,789 B1; Bobo et. al.—U.S. Pat. No. 6,428,234 B1, U.S. Pat. No. 6,592,281 B1, and U.S. Pat. No. 6,637,967 B1; Clark et. al.—U.S. Pat. No. 6,217,603 B1, U.S. Pat. No. 6,428,233 B1, and U.S. Pat. No. 6,592,281 B2; D'Alessio et. al.—U.S. Pat. No. 6,487,191 B1, U.S. Pat. No. 6,283,933 B1, U.S. Pat. No. 6,340,097 B1, U.S. Pat. No. 6,478,191 B1, U.S. Pat. No. 6,494,896 B1, U.S. Pat. No. 6,595,940 B1, U.S. Pat. No. 6,616,019 B2, U.S. Pat. No. 6,896,838 B2, U.S. Pat. No. 6,960,040 B2, US 2003/0039781 A1 and US 2003/0080151 A1; Dunn—EP 0170256; Flesch et. al.—U.S. Pat. No. 3,913,733; Koreska et. al.—U.S. Pat. No. 4,784,506; Leung—U.S. Pat. No. 5,928,611, U.S. Pat. No. 6,099,807, U.S. Pat. No. 6,322,852 B1, U.S. Pat. No. 6,376,019 B1, U.S. Pat. No. 6,676,322 B1, and 7,128,241 B2; Morane et. al.—U.S. Pat. No. 3,964,643; Quintero—U.S. Pat. No. 6,547,467 B2; Quintero et. al.—U.S. Pat. No. 6,705,790 B2, U.S. Pat. No. 7,306,390 B2, and US 2008/0058863 A1; Rivera et. al.—U.S. Pat. No. 6,055,828; Tufts—U.S. Pat. No. 6,536,975 B1; and Voiers et. al.—U.S. Pat. No. 6,425,704 B2, all of which are incorporated herein by reference in their entirety.

Those skilled in the art, based on the state of the art, especially the foregoing patent publications, will readily appreciate the materials that may be used in making the applicator tips, ampoules, filters and applicator body as well as the relative dimensions thereof, particularly for the specific materials to be dispensed. In this regard, it is to be appreciated that the applicators of the present teachings have broad applicability including as applicators of medicaments, cosmetics, cleansing agents, surgical scrubs, paints, adhesives, sealants, and the like, certain of which may have components that are reactive with certain materials used to make the various components of the applicator. For example, depending upon the nature of the cure mechanism of an adhesive composition to be dispensed, one may want to avoid the use of certain types of glass or treated glass in making the ampoules.

Generally speaking, the applicator body will be made of a rigid, but flexible polymeric material which has good flex properties without cracking or breaking. It is also desirable that the polymer material used to make the applicator body be of a translucent or transparent material so as to allow the user to visually inspect the contents to see how much is remaining as the contents are being dispensed. In the case of two-part systems where one part is colored or the two parts, upon intimate mixing form a different color, a transparent or translucent body also allows one to assess how well the contents of the container have been mixed following rupture of the dividing wall or ampoule. Exemplary polymers suitable for use in the practice of the present teachings include, but are not limited to, the polyolefins, such as polyethylene, high density polyethylene, low density polyethylene, linear low density polyethylene, UHMWPE; halogenated polyolefins including the fluorinated versions of the foregoing; polyesters such as polyethylene terephthalate; polyamides; and compatible blends, copolymers and alloys thereof. Especially preferred are the polyolefins, especially polyethylene and polypropylene, particularly HDPE.

The ampoule is generally made of a readily frangible material, one capable of being crushed under finger pressure. Suitable materials include rigid plastics, such as cyclic olefin copolymer, and glass, especially glass.

The filter element may be formed of a porous plastic including those formed of polyurethane, polyesters, polyamides, and polyolefins, such as polyethylene and PTFE. Preferred porous plastics are those made of polyethylene and PTFE, such as those sold by Porex Technologies Corp. (Fairburn, Ga.). Such porous filters typically have an average pore size of about 1 μm to about 500 μm. Alternatively, the filter may be made of paper or another cellulosic material or it may be made from fibers, either natural or synthetic, such as cotton, rayon, nylons, polyesters, polyolefins, and mixtures thereof. The filter body may be composed of a material having random pores, capillaries, a honeycomb material, a material having a woven pattern, etc. The degree of porosity will depend on the materials being used, and can be determined by one of ordinary skill in the art without undue experimentation.

As noted above, the applicator tip may comprise a one-piece element or an assembly of elements, the latter typically having a tip element and an adapter element. It is also to be appreciated that, based on the ultimate construction and application for the applicator, the applicator tip may also function as the filter element. For example, the applicator tip may be formed of a porous material, especially a porous plastic. However, such applicators will not generally employ the bubble breaking technology as bubbles will inherently form upon the emergence of the dispensed liquid from the pores in the porous plastic tip. On there other hand, the prior art porous applicator tips can be converted to take advantage of that feature which includes a receptacle for the shards of the ampoule. Specifically, while such applicator tips generally form an interference fit with the inner lumen of the applicator body and have a cylindrical shape with a flat distal face, the distal end of the porous applicator tip can be formed into a tiered dual cylindrical shape with a smaller diameter cylinder extending from the flat face of the distal end of the conventional applicator tip. Thus, the proximal cylinder forms the interference fit with the lumen of the applicator body while the distal cylinder extends further into the lumen and defines a space between its side wall and the inner wall of the lumen of the applicator body, consistent with the first aspect of the present teachings as discussed above.

Alternatively, the applicator tip may be formed of a nonporous material having a central bore or passageway along its longitudinal axis. These tips may be formed of most any plastic materials, but again, for costs and simplicity of processing are formed of polyolefins, polyurethanes, polyesters or polyamides. On the other hand, where the applicator is to be used in applying a material to a non-rigid and/or contoured surface, especially if it is to be applied to skin, it is preferable that the applicator tip be formed of a supple, low durometer material, which flexes and is able to alter shape consistent with the surface upon which it is acting. Especially suitable materials in this regard are those elastomeric polymers and rubber or rubber-like polymers including ethylene-propylene rubber, ethylene-propylene-diene monomer rubber, elastomeric polyamide, and silicone elastomer, especially silicone elastomer. Depending upon the application, it may be especially desirable to form the applicator tip or, as appropriate the tip element, from a translucent or transparent material as this will allow the user to better view the point of application. As shown in FIG. 3 above, these types of applicator tips have a face 28 having a plurality of projections extending therefrom, typically hemispherical shapes 30 so as to allow the face of the applicator tip to stand off from the surface. If one maintains contact between the applicator tip and the surface upon which it is acting, the height of the projections essentially determine the thickness of the bead or band of material being left on the substrate surface.

Where the applicator tip comprises the tip element and a separate adapter, the applicator tip element may be formed of any of the aforementioned materials for the one-piece tip. The adapter is typically formed of the same material or, especially in the case of an elastomeric tip element, is formed of a more rigid material as one wants to retain the cylindrical shape of the applicator in the tip region in order to avoid altering the shape of the applicator tip as the applicator body is being squeezed. Suitable materials include those discussed above with respect to the applicator tip and the applicator body and also include other polymers such as ABS, polycarbonate, polystyrene, and the like. Preferably, though, the adapter is also a polyolefin, again preferably polyethylene, particularly HDPE, and polypropylene. While the two-part applicator tip assembly is typically two separate parts, those skilled in the art of injection molding will also appreciate that the combined tip element and adapter element may be formed as a single piece in a two step molding process wherein one of the two elements is first molded and then the second element is molded directly to the first, in essence an over-molding type operation.

The applicators may be used as presented above or, as shown in FIGS. 9 and 10, may be inserted into a dispenser handle for improved dispensing precision and control.

The applicators of the present teachings may be used in the dispensing of single part or two or more part fluid compositions, but are especially applicable to two or more part compositions. With the former, the use of dual chambered applicators, especially those having an ampoule is especially important for those applicators which have a porous tip since it is impractical to cap a porous tip. Exemplary materials that may be dispensed include medicaments, cosmetics, cleansing agents, polishes, adhesives, sealants, reagents, indicators, and the like. The applicators are especially suitable for use in medical, dental and veterinarian procedures where the one needs to keep one hand free for other duties while applying the liquid to be dispensed. This is especially so for the application of medical adhesives where the doctor will want to hold the incision site closed with one hand while applying the adhesive with the other.

In those instances where the applicator is to be used in a medical, dental or veterinarian setting, sterilization of the applicator and its contents can be accomplished by techniques known to the skilled artisan, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. A preferred method is electron beam irradiation. In embodiments where a composition is to be used for medical applications, the sterilized composition must show low levels of toxicity to living tissue during its useful life.

While the present invention has been described with respect to aforementioned specific embodiments and examples, it should be appreciated that other embodiments utilizing the concept of the present invention are possible without departing from the scope of the invention. In this regard, since many possible embodiments may be made of the invention without departing from the scope thereof, it is to be understood that all matter herein set forth or shown in the accompanying drawings is to be interpreted as illustrative and not in a limiting sense. Similarly, it is to be appreciated that certain features and combinations and subcombinations thereof are of utility and may be employed without reference to other features and subcombinations. Again, in this regard, it is important to reiterate that each of the features, or specific embodiments thereof, may be incorporated into a state of the art applicator individually or in combinations of one or more of the disclosed. Finally, the present invention is further defined by the claimed elements and any and all modifications, variations, or equivalents that fall within the spirit and scope of the underlying principles embraced or embodied thereby.

We claim:

1. An applicator for liquids and liquid, including viscous, compositions, altogether hereinafter liquid(s), said applicator comprising:
   (I) a hollow applicator body having a dosed distal end, an open proximal end, an inner surface and a longitudinal axis extending along the length of the applicator body, end-to-end, said hollow applicator body defining a lumen and adapted to accept (A) at least one frangible wall capable of dividing the lumen into at least two compartments, (B) at least one frangible ampoule, or (C) both
   (II) an applicator tip or applicator tip assembly associated with and sealing the open proximal end of the applicator body, said applicator tip having a distal end in fluid communication with the lumen of the applicator body, a proximal end from which the liquid is dispelled and a passageway through the applicator tip from the distal end to the proximal end, and
   (III) a filter element having a proximal end, a distal end, and an outer surface, said filter element being within the lumen of the applicator body:
   wherein the applicator tip assembly, if present, is characterized by the combination of an applicator tip and an adapter element, said adapter element having a proximal end to which the distal end of the applicator tip is sealingly secured, a distal end which is sealingly secured within the lumen of the applicator body, and a fluid path in fluid communication with the lumen of the applicator body and the passageway through the applicator tip, and
   wherein, the applicator tip passageway is defined by one or more chambers following and followed by one or more constricted (as compared to the diameter of the chambers) flow paths intermediate said distal and proximal ends thereof.

2. The applicator of claim 1 wherein the the applicator further comprises a tip pin having a proximal end comprising a body, an intermediate portion comprising a stem and a distal end comprising a bulbous member, said pin adapted to be inserted into the proximal end of the passageway and produce a snap-fit seal when the bulbous member enters the chamber.

3. The applicator of claim 1 wherein the portion of the passageway from the chamber to the proximal end of the passageway is conical in cross-section, with the cone base beginning at the chamber and having a diameter of about one half or less of that of the diameter of the chamber and ending at the distal end of the passageway.

4. The applicator of claim 1 having an applicator tip and no adapter.

5. The applicator of claim 1 wherein the applicator is further characterized by a bore in the distal end of the applicator tip or, if present, the adapter element, wherein the bore and filter element are sized so as to allow the bore to receive the proximal end of the filter element while also leaving a gap between the outer surface of the filter element and the inner surface of the applicator body.

6. The applicator of claim 5 wherein the bore in the distal end of the applicator tip or adapter element, as appropriate, is concentric with the passageway through the applicator tip.

7. The applicator of claim 1 wherein the applicator is further characterized by a bore in the distal end of the applicator tip or, if present, the adapter element, which bore is sized smaller than the diameter of the filter element such that the distal surface of the applicator tip or, if present, the adapter element serves as a stop or seat for the filter element and the bore defines a chamber in the distal end of the applicator tip or adapter element, as appropriate.

8. The applicator of claim 7 wherein the bore in the distal end of the applicator tip or adapter element, as appropriate, is concentric with the passageway through the applicator tip.

9. The applicator of claim 1 having an applicator tip assembly.

10. The applicator of claim 9 wherein the applicator tip assembly is further characterized by (1) an applicator tip having a tubular portion extending from the distal end thereof and (2) an adapter element having (I) a distal portion which extends into the lumen of the applicator body and forms a seal therewith, (II) a central bore along its longitudinal axis, (III) a proximal bore in the proximal end thereof and concentric with the central bore and whose diameter is the same as or slightly less than the diameter of the tubular portion of the applicator tip, and (IV) a distal bore concentric with the central bore and whose diameter is the same as or slightly less than the diameter of the filter element, wherein the tubular element of the applicator tip is sealingly engaged in the proximal bore of the adapter and the filter element is sealingly engaged in the distal bore of the adapter.

11. An applicator for liquids and liquid, including viscous, compositions, altogether hereinafter liquid(s), said applicator comprising:
(I) a hollow applicator body having a dosed distal end, an open proximal end, an inner surface and a longitudinal axis extending along the length of the applicator body, end-to-end, said hollow applicator body defining a lumen having (A) at least one frangible wall dividing the lumen into at least two compartments, (B) at least one frangible ampoule therein, or (C) both;
(II) an applicator tip or applicator tip assembly associated with and sealing the open proximal end of the applicator body, said applicator tip having a distal end in fluid communication with the lumen of the applicator body, a proximal end from which the liquid is dispelled and a passageway through the applicator tip from the distal end to the proximal end, and
(III) a filter element having a distal end, a proximal end and an outer surface within the lumen of the applicator body;
wherein (x) the at least one ampoule, if present, contains the liquid or, in the case of a liquid formed of multiple components, at least one of the components of the liquid to be dispensed, (y) the sealed chamber, if present, or at least one of the sealed chambers, if multiple sealed chambers are present, contains the liquid or at least one of the components of the liquid to be dispensed, or (z) both at least one ampoule and at least one sealed chamber are present, the at least one ampoule containing the liquid to be dispensed or at least one of the components of the liquid to be dispensed;
wherein the applicator tip assembly, if present, is characterized by the combination of an applicator tip and an adapter element, said adapter element having a proximal end to which the distal end of the applicator tip is sealingly secured, a distal end which is sealingly secured within the lumen of the applicator body, and a fluid path in fluid communication with the lumen of the applicator body and the passageway through the applicator tip, and
wherein, the applicator tip passageway is defined by one or more chambers following and followed by one or more constricted (as compared to the diameter of the chambers) flow paths intermediate said distal and proximal ends thereof.

12. The applicator of claim 11 wherein the liquid to be dispensed is a two part composition, at least one part contained in the ampoule or the sealed compartment.

13. The applicator of claim 11 wherein the applicator further comprises a tip pin having a proximal end comprising a body, an intermediate portion comprising a stem and a distal end comprising a bulbous member, said pin adapted to be inserted into the proximal end of the passageway and produce a snap-fit seal when the bulbous member enters the chamber.

14. The applicator of claim 11 wherein the portion of the passageway from the chamber to the proximal end of the passageway is conical in cross-section, with the cone base beginning at the chamber and having a diameter of about one half or less of that of the diameter of the chamber and ending at the distal end of the passageway.

15. The applicator of claim 11 having an applicator tip and no adapter.

16. The applicator of claim 11 wherein the applicator is further characterized by a bore in the distal end of the applicator tip or, if present, the adapter element, wherein the bore and filter element are sized so as to allow the bore to receive the proximal end of the filter element while also leaving a gap between the outer surface of the filter element and the inner surface of the applicator body.

17. The applicator of claim 16 wherein the bore in the distal end of the applicator tip or adapter element, as appropriate, is concentric with the passageway through the applicator tip.

18. The applicator of claim 11 wherein the applicator is further characterized by a bore in the distal end of the applicator tip or, if present, the adapter element, which bore is sized smaller than the diameter of the filter element such that the distal surface of the applicator tip or, if present, the adapter element serves as a stop or seat for the filter element and the bore defines a chamber in the distal end of the applicator tip or adapter element, as appropriate.

19. The applicator of claim 18 wherein the bore in the distal end of the applicator tip or adapter element, as appropriate, is concentric with the passageway through the applicator tip.

20. The applicator of claim 11 having an applicator tip assembly.

21. The applicator of claim 20 wherein the applicator tip assembly is further characterized by (1) an applicator tip having a tubular portion extending from the distal end thereof and (2) an adapter element having (I) a distal portion which extends into the lumen of the applicator body and forms a seal therewith, (II) a central bore along its longitudinal axis, (III) a proximal bore in the proximal end thereof and concentric with the central bore and whose diameter is the same as or slightly less than the diameter of the tubular portion of the applicator tip, and (IV) a distal bore in the distal end concentric with the central bore and whose diameter is the same as or slightly less than the diameter of the filter element, wherein the tubular element of the applicator tip is sealingly engaged in the proximal bore of the adapter and the filter element is sealingly engaged in the distal bore of the adapter.

22. The applicator of claim 11 wherein the liquid to be dispensed is a two part composition and the applicator includes both a frangible wall and an ampoule, at least one part of the two part composition being contained in the ampoule.

23. The applicator of claim 22 wherein the ampoule is within the sealed compartment.

24. The applicator of claim 23 wherein the sealed compartment containing the ampoule also contains the second part of the two part composition.

* * * * *